(12) United States Patent
Richter et al.

(10) Patent No.: US 8,611,828 B2
(45) Date of Patent: Dec. 17, 2013

(54) SYSTEM AND METHODS FOR SELF-POWERED, CONTACTLESS, SELF-COMMUNICATING SENSOR DEVICES

(76) Inventors: Wolfgang Richter, Starnberg (DE); Faranak Zadeh, Vancouver (CA)

(*) Notice: Subject to any disclaimer, the term of this patent is extended or adjusted under 35 U.S.C. 154(b) by 275 days.

(21) Appl. No.: 13/174,613

(22) Filed: Jun. 30, 2011

(65) Prior Publication Data

US 2012/0004523 A1 Jan. 5, 2012

Related U.S. Application Data

(60) Provisional application No. 61/360,115, filed on Jun. 30, 2010.

(51) Int. Cl.
*H04B 17/00* (2006.01)

(52) U.S. Cl.
USPC ...... 455/67.11; 455/66.1; 455/100; 455/63.1; 607/46

(58) Field of Classification Search
USPC .............. 455/67.11, 66.1, 100, 63.1, 3.06; 607/46; 310/339, 319; 324/727
See application file for complete search history.

(56) References Cited

U.S. PATENT DOCUMENTS

| | | | |
|---|---|---|---|
| 6,528,782 B1 * | 3/2003 | Zhang et al. | 250/226 |
| 6,809,462 B2 * | 10/2004 | Pelrine et al. | 310/319 |
| 7,135,637 B2 * | 11/2006 | Nishitani et al. | 84/723 |
| 7,538,445 B2 * | 5/2009 | Kornbluh et al. | 290/53 |
| 7,691,806 B2 * | 4/2010 | Collier et al. | 514/18.8 |
| 7,875,791 B2 * | 1/2011 | Leonov et al. | 136/212 |
| 7,976,968 B2 * | 7/2011 | Siu et al. | 429/2 |
| 7,982,371 B1 * | 7/2011 | Anand et al. | 310/339 |
| 8,099,054 B2 * | 1/2012 | Tabe | 455/63.1 |
| 8,381,601 B2 * | 2/2013 | Stumpf | 73/862.041 |
| 2002/0130673 A1 * | 9/2002 | Pelrine et al. | 324/727 |
| 2005/0003386 A1 * | 1/2005 | Bazan et al. | 435/6 |
| 2007/0257490 A1 * | 11/2007 | Kornbluh et al. | 290/53 |
| 2008/0314429 A1 * | 12/2008 | Leonov | 136/201 |
| 2009/0157141 A1 * | 6/2009 | Chiao et al. | 607/46 |
| 2012/0043858 A1 * | 2/2012 | Mahapatra et al. | 310/339 |
| 2012/0293047 A1 * | 11/2012 | Wang et al. | 310/339 |

* cited by examiner

*Primary Examiner* — Minh D Dao

(57) ABSTRACT

The innovation introduces a new kind of smart biological-sensing controller, based on silicon and/or flexible polymer printed electronics. The purpose of the device is to monitor and/or control biological signals of living organisms (for example, microbes, bacteria, insects, plants, animals, and people). Embedded in a system, the innovation can work contactless and battery-free since it is self-powered, wirelessly self-communicating without the use of electromagnetic waves like radio frequencies (RF), infrared or other electromagnetic technologies. Instead, the innovation uses alternating electric fields for powering, measuring and communicating, and introduces an innovative new method of mobile vital signs monitoring.

6 Claims, 3 Drawing Sheets

Figure 1:
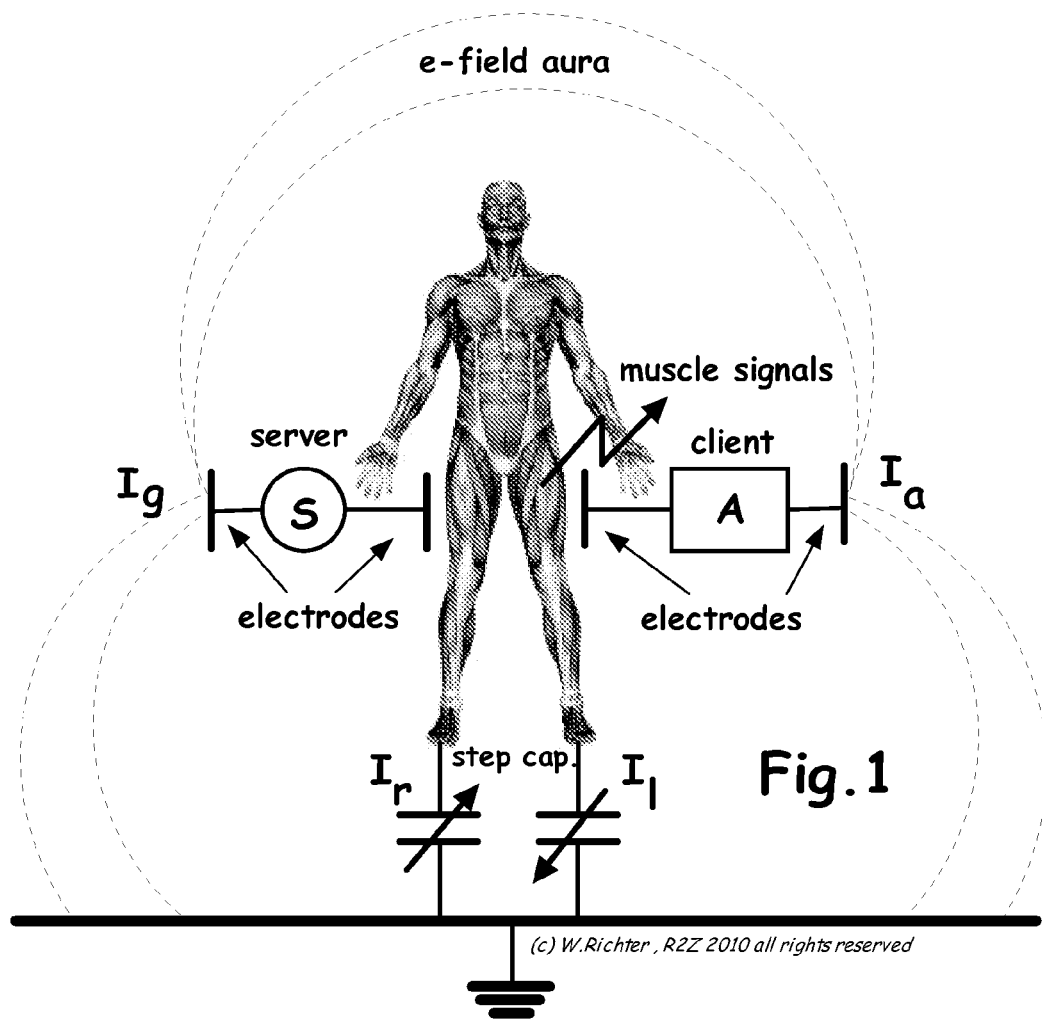

SYSTEM AND METHODS FOR SELF-POWERED, CONTACTLESS, SELF-COMMUNICATING SENSOR DEVICES

PRIORITY

This application claims priority to Provisional Application No. 61/360,115 filed on Jun. 30, 2010, the entire contents of which are incorporated herein by references.

COPYRIGHT NOTICE

A portion of the disclosure of this patent document contains material which is subject to copyright or mask work protection. The copyright or mask work owner has no objection to the facsimile reproduction by anyone of the patent document or the patent disclosure, as it appears in the Patent and Trademark Office patent file or records, but otherwise reserves all copyright or mask work rights whatsoever.

BRIEF SUMMARY OF THE INVENTION

As it now state of the art, smart sensors used for measuring vital signs come in a wide variety, but they all need to be powered with electric energy to do their measurement assignments. For communicating, a network is used, which can be wired or wireless. If sensors work wirelessly, most of them are using radio frequencies in a higher range, up to several gigahertz. It is well known that microwaves warm up tissue and cells of the human dermis/body. The smart sensors work on batteries which need to be replaced or recharged from time to time depending on the power consumption of each sensor. Complicated server software is needed to guaranty collision-free functioning in a smart sensor network. Vital signs, especially those of people, are barely to register on the human skin. In the past, special electrodes were needed to make a contact and connection to these vital signs, as well to any smart sensor, which has to measure them. Such electrodes are sticky and painful to remove; most of them contain chemicals in order to create a better changeover between the electrode material and the human dermis. If it is necessary to measure vital signs other than the bio-electrical ones (such as movements, sounds, forces), special sensor elements have to be added like gyroscopes and accelerometers, microphones or force-changing resistors (FSR).

A single chip, which can be realized either by siliconizing and/or as printed electronic on polymer foil, is self-powered by an alternating electric field within its reach. The device is self-communicating over the same field, collision free and self-organized within sensor networks. The technology is printable on polymer either as a hybrid with silicon flip chip(s) or as full printed electronics. It works contactless and uses physical effects for multi-sensing purposes without any external added sensing elements.

STATE OF THE ART

Sending data via the human skin was first announced by Robinson, followed by Thomas Guthrie Zimmerman in his Masters work for M.I.T., February 1980, Microsoft claimed that it is possible to power devices over the human skin, but for a different purpose. Energy harvesters can replace batteries, but they use generators that work with thermic energy (body heat) or vibration (piezo or dynamo magnetic effect) or other, mostly mechanical sources. Solar cells can charge batteries from a light source.

THE INNOVATION UNDERLYING PRINCIPLE

The innovation here described uses a different method: alternating electric fields can generate a type of synthetic aura around a person's body with a certain frequency. Electrodes can collect the e-field(s) with their capacitance and rectifiers can charge buffers like capacitors, accumulators, gold caps or others with electrical DC energy, which can be used to power electrical circuits connected to the buffer, continuously or periodically.

As a rectifying diode is also a kind of dynamic resistor and capacitor, in which its resistance and capacitance depends on the voltage or polarity, it works also as a filter in association with the connected buffer. So there are cutoff frequencies and resonance frequencies that create different output voltage depending on the input level and input frequency of the energy provided by the electric field(s).

Functional Principle

An e-field generator circuit is placed near a human body. The electric field(s) spread(s) out in a synthetic aura over the body's skin (dermis). A first, the invention underlying device is also within reach of these electric fields and the human body, connected to at least one (pair) of electrode(s).

The innovation's harvester electrode(s) collect(s) the field lines from the alternating e-field(s), rectifies them, brings them in resonance and charges at least one buffer.

An instrumentation amplifier is powered with this energy. Its inputs have electrodes near the human body that are charged by vital signs as well as by the frequency of the electric generated field.

As the instrumentation amplifier has plus and minus inputs, equal signals (from the e-field) are subtracted to zero and only differential signals will be amplified. The sensing electrodes can be discharged to a virtual ground provided by the energy harvester. The amplified bio-signal can be filtered and modulated to a carrier that sends back to an analysis device using the same (or other) e-field(s).

This kind of data can also be stored or transmitted to other external interpretation units or systems.

If a living organism moves in an e-field, it also alters the e-field in relation to capacitive means against ground or other objects. Changing the capacitive coupling against both, results that the power collected by the e-field harvester is varying according to environmental circumstances, which creates also information about the movement itself.

FIG. 1 shows the working principle: the invention circuit A is near a person's muscle (upper left leg) while the e-field generator S is carried or placed by the person's right side. The electric field(s) spread(s) out over the person's body but also against ground so that electrical current Ig is measurable from the e-field generator to ground and to the human body over the right leg to ground (Ir), over the left leg to ground (Il) and over the sensing device innovation to ground (Ia). If a person lifts a foot, the capacitance against ground decreases and the intensity of the currents are different than before. Analyzing these effects can replace pedometers or other monitoring devices that have to take care of movements.

Figure 2:
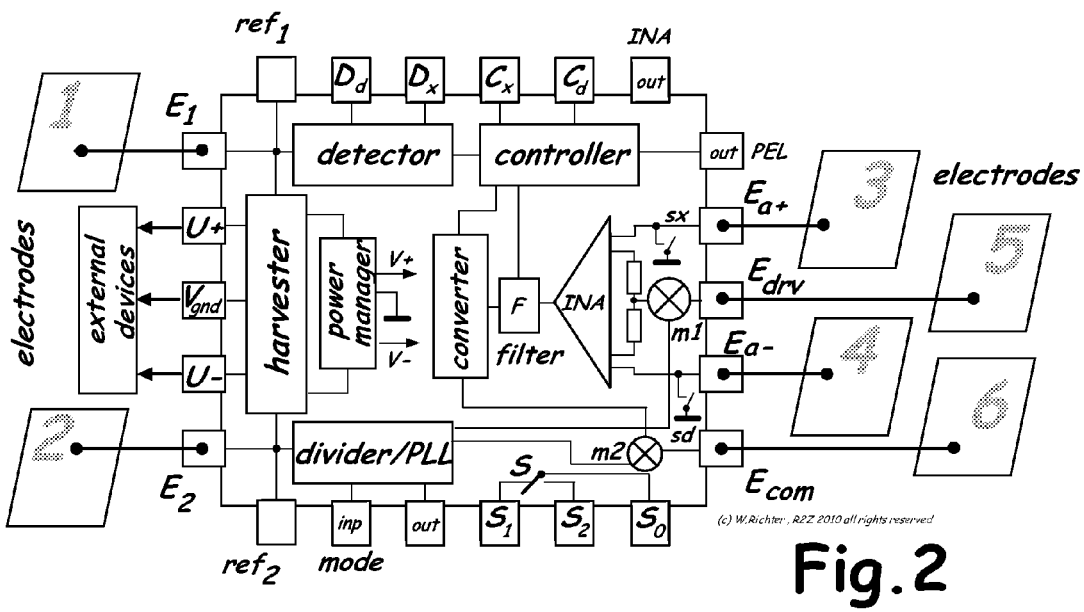

A First Circuit Underlying the Innovation:

FIG. 2 shows a picture of the components as a block schematic that can be realized in silicon or as printed electronic on polymer or other (preferably flexible) material.

The conductive pads E1 and E2 are connected to electrodes that are able to collect alternating electric fields. (They can be of any conductive material, any size or any shape.) These electrodes can be applied directly (via contact) or indirectly (contactless) to the dermal skin of the object that is to be monitored. If an (alternating) E-Field is present and in reach, an energy harvester collects, filters and generates DC power out of this e-field in an the invention underlying method.

If necessary or wanted, external devices can be powered connected to the pads V+, V− and/or Vgnd (outputs).

The frequency(s) of the alternating E-Field(s) can be used internally as a clock or as a transmitting carrier so there are means for manipulating them.
Frequencies can be divided or multiplied (e.g. PLL), therefore the innovation provides related sub circuits.

The pads, Ea+ and Ea− are the analog sensing inputs and internally connected to an instrumentation amplifier (INA) for measuring differential charges provided by muscles, heart, brain or other sources.

A controllable filter helps to select wanted signals. The circuit is also able to generate its own electric field and provide this on the Ecom pad. A switch section S0, S1, S2 provides powerless switching (on/off) of external devices or signals.

Finally, means create a so-called Peripheral Extension Link on the PEL pad for bidirectional communication with external devices.

The modulator's product consists of the measured data (e.g. biological vital signs), mixed with the harvester e-field information (strength frequency etc.), and/or carrier and/or envelope, and/or control signals.

The complete device can be also used as a kind of development kit where pads can be connected with each other to create different functions. The invention underlying control unit is at least programmable via the alternating electric field. It controls the internal chip timing, the amplification gain, the filtering, the modulator, the harvester, the buffers and dividers/PLLs as well as the switchboard(s).

A First Application

Figure 3:
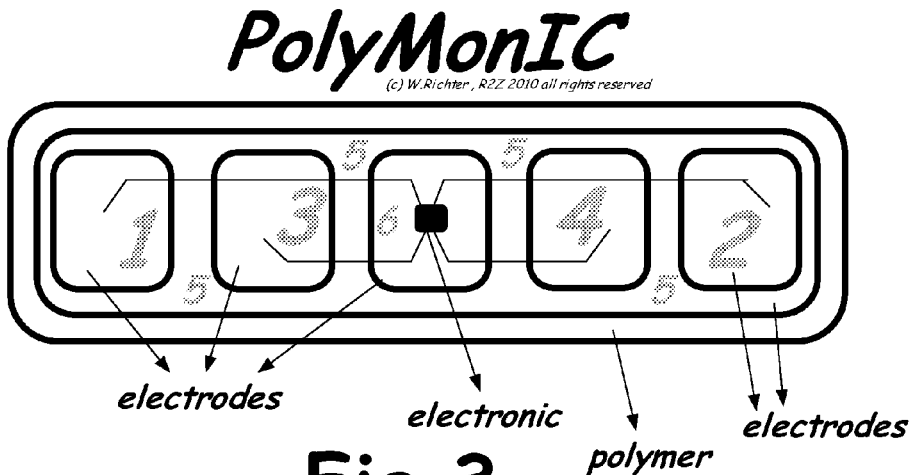

The invention is attached to a patch (FIG. 3) that a person can carry on any position on his/her body that needs to be monitored (for example, the heart). The user carries a watch-like device on the wrist, (so called Bi-O-Watch) which functions as a server. It creates a least one alternating electric field and provides a detector for receiving data from the invention device. The patch functions as a kind of client and can be made from polymer or other preferably flexible material. If the electric field reaches the electrodes E1 and E2, the harvester in the circuit starts working, generating power. The instrumentation amplifier (INA) collects the charges of the human electrocardiogram (ECG) and forces the divider/PLL in the chip to create transferable frequencies (or data) related to the human heart's typical amplitudes. The detector in the Bi-O-Watch Server receives these frequencies and filters and generates the original heart signal (or other data or vital signs) out of them, which can be interpreted or shown on a display, or transferred over a network (such as the internet).

Multiple client patches can also be placed near other parts of the body, such as the spine, the muscles of the limbs, or used as a kind of headband for monitoring brain signals (EEGs).

As the detector of a first patch "hears" the signals from other patches nearby, at the same time the control unit causes the divider/PLL to create different (communication) E-Field frequencies.

Any device also contains a unique ID that makes it easier for any server to distinguish between them.

The Invention Underlying Further Applications a) Toys: special kinds of human motions are gestures. A toy (e.g. plush, robot, doll or others) which consists of at least one device of the innovation can sense these gestures and react on approaching limbs or fingers of a player. Differences in E-field absorption between electrodes will be detected and can cause the toy to "react" on gestures by moving (electro mechanical) parts (head, limbs, wheels, joints etc.) or by creating any kind of feedback (sound, light and/or other effects). At the other end, a toy can detect the appearance of a person, or a sleeping child's vital signs can be monitored e.g. by its teddy bear (heartbeat, breathing, movements, etc).

The innovation's harvester generates enough power that LEDs can shine with no additional power source when they are within the reach of a generated E-Field. This can be used in toys or board games, video consoles, online games, action figures and play sets, for effects in relation to people playing with these items.

b) Fitness: users and/or athletes can train their muscles by exercising them with or without fitness equipment while the innovation monitors forces, movements, speed and/or other physical effects related to the human body's unique electrical signals (brain, heart, muscles), body sounds (breathing, coughing etc.) or movements and impacts to joints or bones. The monitored signals can be analyzed and displayed over a network and used as training support on feedback devices such as (TV-) screens or mobile phones.

c) Wellness: measuring stress, strenuous activities, upset stomachs, high temperatures, skin resistance (AC e-field method, contactless), sleep-related activities and much more can be achieved by the innovation.

d) Veterinary: the said device can be mounted in a kind of diagnostic glove that can be used by a person to check the vital signals of a variety of animals (cattle, horses, dogs, etc). The e-field generator and analysis circuit can be carried by the person or a unit that the animal is standing on or anyhow near the animal.

e) Sports: the innovation helps at least one athlete to work on the mental part of his or her game or discipline by providing means toward greater self-awareness achieved through meditation. Brain waves can be monitored by the innovation device and will provide the basis for an effective mental training regime and feedback method. Attached to a patch, with a matrix of chemicals (marker) in a form of a Band-Aid, the innovation can be used for doping tests. If the sport activities last longer, it is possible to create pseudo checkpoints where at least one E-Field is provided. If the athlete comes into such a field, his/her device starts working and transmits the measured results without interrupting the sport.

f) Medical: the innovation is effective for any type of implant. Also bandages, cobbles, patches or adhesive tapes for allergy testing (similar to the doping matrix), doping and drug use control, pregnancy monitoring, and/or disease monitoring from cancer, HIV or other illnesses. Electrophoretically drug delivery and wound management can be also realized with the innovation.

Figure 4:
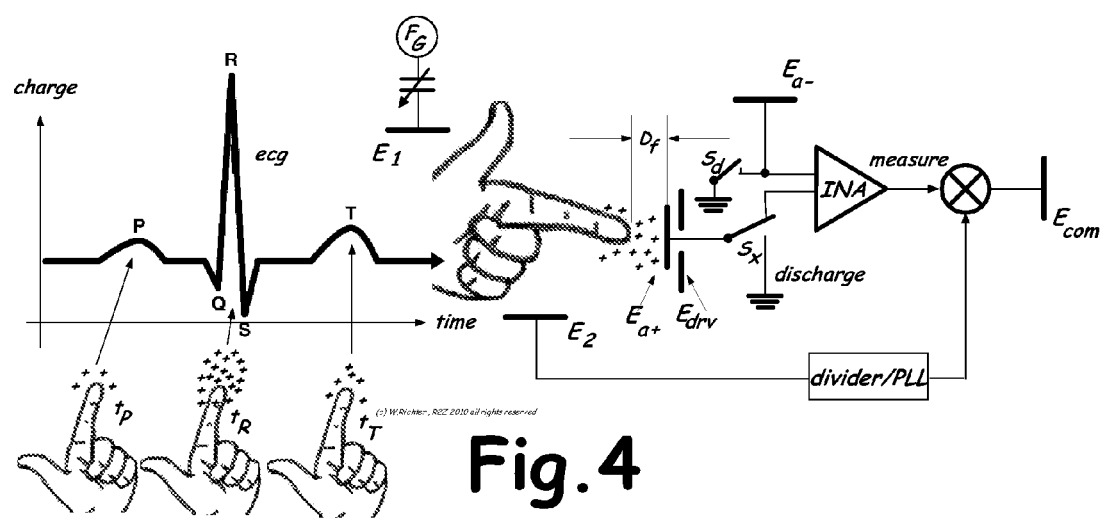

Since all of these applications need no batteries in the innovation's circuit, it can additional transmit a kind of "OK signal" all the time to make sure that the system is (proper) working, if influenced by at least one alternating E-Field.

g) Consumer: the invention allows new kind of remote control devices. The innovation underlying patches can be implemented as foils in (car-) seats, beds or wheelchairs (free of any maintenance) or other furniture. As the underlying circuit work only with persons and E-Fields in reach, the innovation can be also used for proximity detection, specially in combination with h) Biometrics: FIG. 4 shows that a human's heartbeat appears as electrical charges over the dermis which can influence the innovation's sensing electrode(s). The heart signals can be interpreted to identify a human by an external (or build in) algorithm or means for numerous purposes.

What is claimed is:

1. The system for self powered and self communicating vital signs measurements based on silicone and/or polymer using at least one electrical field for powering, measuring and communicating, said system comprising:
   a stationary device for generating at least one electrical field alternating in frequency;
   means for receiving frequencies over said alternating electrical field; and
   plurality of flexible polymer printed electrodes foil for integrating silicon chips through said at least one electrical field alternating in frequency, said flexible polymer printed electrodes foil to be place in close proximity to a user for contactless vital sign measurements;
   wherein said alternating electrical field creating a phase locked loop for changing the frequencies either by dividing or by multiplying.

2. The system according to claim 1 further comprising a modulator for mixing fixed data (ID numbers and constant parameters), measurement values from various vital signs and body signals (at least one carrier from a server's e-field divided or multiplied) as well as an output driver for sending the modulated data to at least one electrode.

3. The system according to claim 1 further comprising means for supplying power to external devices with at least one positive and one negative voltage as well as a virtual ground.

4. The system according to claim 1 further comprising electronic switches integrated for switching on or off external electrical or electronic components.

5. The system according to claim 1 further comprising a server for generating at least one alternating electric field and at least one client (polyMonIC) for measurement of vital signs contactless and battery-free, wherein said server further comprising at least one analytical means for computing the received data.

6. The system according to claim 1 further comprising an electrical energy harvester powered by at least one alternating electric field creating at least dual output voltage for driving instrumentation amplifiers or other electronic parts or devices.

* * * * *